United States Patent [19]

Löher et al.

[11] Patent Number: 5,129,941
[45] Date of Patent: Jul. 14, 1992

[54] HETEROCYCLICALLY SUBSTITUTED SULFONYLUREAS, AND THEIR USE AS HERBICIDES OR PLANT GROWTH REGULATORS

[75] Inventors: Heinz-Josef Löher, Hofheim am Taunus; Lothar Willms, Hillscheid; Michael Frey, Neusäss; Klaus Bauer, Hanau; Hermann Bierigner, Eppstein/Taunus, all of Fed. Rep. of Germany

[73] Assignee: Hoechst Aktiengesellschaft, Frankfurt am Main, Fed. Rep. of Germany

[21] Appl. No.: 553,702

[22] Filed: Jul. 17, 1990

[30] Foreign Application Priority Data

Jul. 19, 1989 [DE] Fed. Rep. of Germany ....... 3923819
Jun. 1, 1990 [DE] Fed. Rep. of Germany ....... 4017664

[51] Int. Cl.⁵ .................. A01N 43/54; C07D 239/34; C07D 239/42; C07D 239/47
[52] U.S. Cl. ..................................... 71/92; 544/319; 544/320; 544/321; 544/324; 544/323; 544/327; 544/331; 544/332
[58] Field of Search .................... 71/92; 544/319, 320, 544/321, 324, 323, 327, 331, 332

[56] References Cited

U.S. PATENT DOCUMENTS

| | | | |
|---|---|---|---|
| 3,267,139 | 8/1966 | Lafferty | 260/556 |
| 4,440,565 | 4/1984 | Willms et al. | 71/93 |
| 4,492,598 | 1/1985 | Willms et al. | 71/93 |
| 4,540,782 | 9/1985 | Meyer | 544/194 |
| 4,601,747 | 7/1986 | Willms et al. | 71/92 |
| 4,718,937 | 1/1988 | Willms et al. | 71/93 |

FOREIGN PATENT DOCUMENTS

| | | |
|---|---|---|
| 11811/83 | 9/1983 | Australia. |
| 0061661 | 10/1982 | European Pat. Off. . |
| 0070804 | 1/1983 | European Pat. Off. . |
| 0071958 | 2/1983 | European Pat. Off. . |
| 0085276 | 8/1983 | European Pat. Off. . |
| 0087780 | 9/1983 | European Pat. Off. . |
| 0131258 | 1/1985 | European Pat. Off. . |
| 0353641 | 2/1990 | European Pat. Off. . |
| 2257240 | 5/1974 | Fed. Rep. of Germany . |
| 3243533 | 6/1983 | Fed. Rep. of Germany . |
| 2110689 | 6/1983 | United Kingdom . |

Primary Examiner—John M. Ford
Attorney, Agent, or Firm—Curtis, Morris & Safford

[57] ABSTRACT

Sulfonylureas of the formula $$R^1-Y-A-NR^2-SO_2-NH-\overset{Z}{\underset{\|}{C}}-NR^3R^4 \quad (I)$$

where
A is a bond or a $C_1$–$C_{10}$-hydrocarbon radical,
$R^1$ is an optionally unsaturated hydrocarbon radical which is optionally substituted by halogen, optionally unsaturated alkoxy, alkylthio, alkylsulfonyl or alkylsulfinyl, cycloalkyl, optionally substituted phenyl or a heterocycle, or is optionally substituted phenyl, NRR' with R and R' being alkyl, alkoxy or alkylene (cyclic with N),
Y is S, SO or $SO_2$,
$R^1$ is optionally unsaturated alkoxy which is optionally substituted, or is cycloalkoxy, cycloalkenyloxy, cyclopropylmethyloxy, epoxypropyloxy, furfuryloxy, tetrahydrofurfuryloxy or optionally substituted phenoxyalkoxy or phenoxy,
$R^3$ is alkyl which is optionally unsaturated, or is alkoxy,
$R^4$ is optionally substituted pyrimidinyl, pyrimidinylmethyl, pyrimidinyl with a fused-on cyclopentane, oxolane, oxolene, oxane, pyridine or pyrazine ring or purinyl or triazolyl, and
Z is O or S, have herbicidal and/or plant-growth-regulatory properties.

19 Claims, No Drawings

HETEROCYCLICALLY SUBSTITUTED SULFONYLUREAS, AND THEIR USE AS HERBICIDES OR PLANT GROWTH REGULATORS

It is known that heterocyclically substituted alkylsulfonylureas have herbicidal and plant-growth-regulating properties (see EP-A 061,661, EP-A 071,958, EP-A 131,258, German Offenlegungsschrift 3,243,533). However, some of these have disadvantages when used, such as, for example, high persistence or insufficient selectivity in important crops.

Novel heterocyclic sulfonylureas which have advantageous herbicidal properties have now been found.

The present invention relates to compounds of the general formula (I)

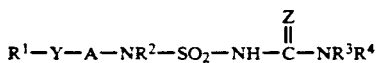

where
- A is a direct bond or a saturated or unsaturated, unbranched or branched $C_1-C_{10}$-hydrocarbon radical, preferably a direct bond or a $C_2-C_{10}$-hydrocarbon radical, such as, in particular, a radical of the formula $CH_2CH_2$, $CRR'$, $CH_2CHR$ or $CH_2CRR'$, where R and R' independently of one another are $C_1-C_4$-alkyl or $C_2-C_4$-alkenyl,
- $R^1$ is $C_1-C_8$-alkyl, $C_2-C_8$-alkenyl, $C_2-C_8$-alkynyl, $C_3-C_8$-cycloalkyl, $C_5-C_8$-cycloalkenyl or one of the above five radicals which is monosubstituted or polysubstituted by halogen or by those radicals which are selected from the group comprising $C_1-C_6$-alkoxy, $C_2-C_6$-alkenyloxy, $C_2-C_6$-alkynyloxy, $C_1-C_8$-alkylthio, $C_1-C_6$-alkylsulfinyl, $C_1-C_6$-alkylsulfonyl, $C_3-C_6$-cycloalkyl, a radical of a three-membered to six-membered saturated heterocycle with one oxygen atom in the ring, furyl, phenyl and a phenyl radical which is monosubstituted or polysubstituted by radicals from the group comprising halogen, CN, $C_1-C_4$-alkyl-, $C_1-C_4$-alkoxy, $C_1-C_4$-haloalkyl, such as $CF_3$, or by ($C_1-C_4$-alkoxy)carbonyl and nitro, or phenyl or a phenyl radical which is monosubstituted or polysubstituted by radicals from the group embracing halogen, CN, $C_1-C_4$-alkyl, $C_1-C_4$-alkoxy, $C_1-C_4$-haloalkyl, such as $CF_3$, or by ($C_1-C_4$-alkoxy)carbonyl and nitro, or a radical of the formula $-NR^5R^6$, where $R^5$ and $R^6$ independently of one another are hydrogen or $C_1-C_8$-alkyl, or one of the radicals $R^5$ or $R^6$ is $C_1-C_4$-alkoxy, or $R^5$ and $R^6$ together form an alkylene chain $-(CH_2)_n-$ with n being 2 to 7;
- Y is S, SO or $SO_2$, preferably $SO_2$,
- $R^2$ is $C_1-C_8$-alkyloxy, $C_2-C_8$-alkenyloxy, $C_2-C_8$-alkynyloxy or one of the above 3 radicals which is monosubstituted or polysubstituted by halogen or by radicals from the group comprising $C_1-C_6$-alkoxy, $C_2-C_6$-alkenyloxy, $C_2-C_6$-alkynyloxy, $C_1-C_6$-alkylthio, $C_1-C_6$-alkylsulfinyl, $C_1-C_6$-alkylsulfonyl, ($C_1-C_6$-alkoxy)carbonyl, phenoxycarbonyl, benzyloxycarbonyl and phenyl, or $R^2$ is $C_3-C_8$-cycloalkyloxy which is unsubstituted or monosubstituted or polysubstituted by halogen, or monosubstituted or disubstituted by $C_1-C_4$-alkoxy or $C_1-C_4$-alkylthio; $C_5-C_8$-cycloalkenyloxy, cyclopropylmethyloxy, epoxypropyloxy, furfuryloxy, tetrahydrofurfuryloxy, phenoxy-$C_1-C_6$-alkyloxy, phenoxy or one of the last two abovementioned radicals which is substituted in the phenyl ring by halogen, $C_1-C_4$-alkyl, $C_1-C_4$-alkoxy or nitro,
- $R^3$ is H, $C_1-C_8$-alkyl, $C_2-C_8$-alkenyl, $C_2-C_8$-alkynyl- or $C_1-c_4$-alkoxy,
- $R^4$ is a radical of the formula

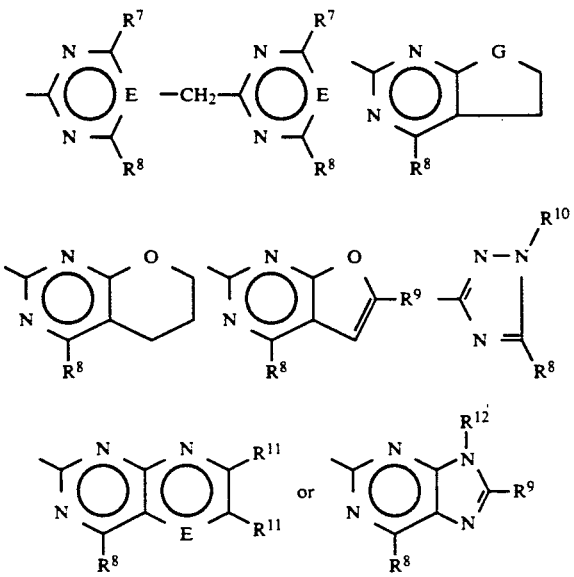

$R^7$ and $R^8$ independently of one another are H, halogen, $C_1-C_6$-alkyl, $C_1-C_6$-alkoxy, $C_1-C_6$-alkylthio or one of last three abovementioned radicals which is monosubstituted or polysubstituted by halogen or monosubstituted or disubstituted by $C_1-C_4$-alkoxy or $C_1-C_4$-alkylthio, or are a radical $NR^{13}R^{14}$, $C_3-C_6$-cycloalkyl, $-OCHR^{15}COOR^{16}$, $C_3-C_5$-alkenyl, $C_2-C_4$-alkynyl, $C_3-C_5$-alkenyloxy or $C_1-C_4$-alkynyloxy, $R^9$ is hydrogen or $C_1-C_4$-alkyl, $R^{10}$ is $C_1-C_4$-alkyl, $-CHF_2$ or $-CH_2CF_3$, $R^{11}$ radicals independently of one another are H, $C_1-C_4$-alkyl, $C_1-C_4$-alkoxy or halogen, $R^{12}$ is hydrogen, $C_1-C_4$-alkyl, $CHF_2$ or $CH_2CF_3$, $R^{13}$ and $R^{14}$ independently of one another are H, $C_1-C_4$-alkyl, $C_2-C_4$-alkenyl or $C_3-C_4$-alkynyl, $R^{15}$ is hydrogen or $C_1-C_4$-alkyl, $R^{16}$ is hydrogen or $C_1-C_4$-alkyl, E is CH or N, G is $CH_2$ or O, and Z is O or S, preferably an oxygen atom, and salts thereof.

The compounds of the formula (I) can form salts in which the hydrogen of the $-SO_2-NH-$ group is replaced by a cation which is suitable for agriculture. Examples of these salts are metal salts, in particular alkali metal salts and alkaline earth metal salts, and optionally alkylated ammonium or organic amine salts. They are preferably prepared from the compounds of the formula (I) in solvents which are inert under the reaction conditions, such as water, methanol or acetone, at temperatures from 0 to 100° C. Examples of suitable bases for the preparation of the salts according to the invention are alkali metal carbonates, such as potassium carbonate, and alkali metal hydroxides and alkaline earth metal hydroxides, and also ammonia and ethanolamine.

Compounds of the formula (I) according to the invention in which

R$^1$ is C$_1$-C$_4$-alkyl, a C$_1$-C$_4$-alkyl radical which is monosubstituted or polysubstituted by halogen or monosubstituted or disubstituted by C$_1$-C$_4$-alkoxy, C$_2$-C$_3$-alkenyloxy, C$_2$-C$_3$-alkynyloxy, C$_1$-C$_4$-alkylthio, C$_1$-C$_4$-alkylsulfinyl, C$_1$-C$_4$-alkylsulfonyl, phenyl or a phenyl radical which is monosubstituted to trisubstituted by radicals from the group comprising halogen, C$_1$-C$_4$-alkyl, C$_1$-C$_4$-alkoxy, CF$_3$, (C$_1$-C$_4$-alkoxy)carbonyl and nitro, or are C$_3$-C$_8$-cycloalkyl or a C$_3$-C$_8$-cycloalkyl radical which is monosubstituted or polysubstituted by halogen or monosubstituted to disubstituted by C$_1$-C$_4$-alkoxy or C$_1$-C$_4$-alkylthio, or R$^1$ is C$_5$-C$_8$-cycloalkenyl, cyclopropylmethyl, epoxypropyl, furfuryl, tetrahydrofurfuryl, benzyl, phenyl, or is a benzyl or phenyl radical which is substituted in the phenyl ring by one or more radicals from the group comprising halogen, C$_1$-C$_4$-alkyl, C$_1$-C$_4$-alkoxy, CF$_3$, (C$_1$-C$_4$-alkoxy)carbonyl and nitro, or R$^1$ is a radical of the formula NR$^5$R$^6$, where R$^5$ is C$_1$-C$_4$-alkyl and R$^6$ is hydrogen or C$_1$-C$_4$-alkyl, or R$^5$ and R$^6$ together form an alkylene chain —(CH$_2$)$_n$— with n being 4 or 5, are of particular interest.

Compounds of the formula (I) according to the invention in which

R$^2$ is C$_1$-C$_4$-alkyloxy, a C$_1$-C$_4$-alkyloxy radical which is monosubstituted or polysubstituted by halogen or monosubstituted or disubstitued by C$_1$-C$_4$-alkoxy, C$_2$-C$_4$-alkenyloxy, propargyloxy, C$_1$-C$_4$-alkylthio, C$_1$-C$_4$-alkylsulfinyl, C$_1$-C$_4$-alkylsulfonyl, (C$_1$-C$_4$-alkoxy)carbonyl, phenoxycarbonyl, benzyloxycarbonyl or phenyl, or is C$_3$-C$_8$-cycloalkyloxy, are of particular interest.

Compounds of the formula (I) according to the invention in which

R$^4$ is a radical of the formula

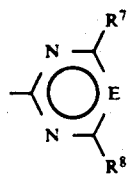

and

R$^7$ and R$^8$ independently of one another are halogen, C$_1$-C$_4$-alkyl, C$_1$-C$_4$-alkoxy, C$_1$-C$_4$-alkylthio or one of the last three abovementioned radicals which are monosubstituted or polysubstituted by halogen or monosubstituted or disubstituted by C$_1$-C$_4$-alkoxy or C$_1$-C$_4$-alkylthio, or R$^7$ and R$^8$ are a radical NR$^{13}$R$^{14}$, C$_3$-C$_6$-cycloalkyl, —OCHR$^{15}$COOR$^{16}$, allyl, propargyl, allyloxy or propargyloxy, R$^{13}$ and R$^{14}$ independently of one another are H or C$_1$-C$_4$-alkyl, R$^{15}$ is H or C$_1$-C$_4$-alkyl, R$^{16}$ is C$_1$-C$_4$-alkyl, and E is CH or N, are furthermore of particular interest.

Preferred compounds of the formula (I) are those in which

A is a direct bond or a radical of the formula —CH$_2$—CH$_2$—,

R$^1$ C$_1$-C$_4$-alkyl, a C$_1$-C$_4$-alkyl radical which is monosubstituted or polysubstituted by halogen or monosubstituted to disubstituted by C$_1$-c$_4$-alkoxy, or, in the event that A is a direct bond, R$^1$ is also preferably a radical of the formula NR$^5$R$^6$ where R$^5$ is C$_1$-C$_4$-alkyl and R$^6$ is hydrogen or C$_1$-C$_4$-alkyl, or R$^5$ and R$^6$ together form an alkylene chain —(CH$_2$)$_n$— with n being 4 or 5, or, in the event that A=—CH$_2$CH$_2$—, R$^1$ is also C$_3$-C$_8$-cycloalkyl which is unsubstituted or monosubstituted or polysubstituted by halogen, or is benzyl, phenyl, or a benzyl or phenyl radical which is monosubstituted or polysubstituted in the phenyl ring by halogen, C$_1$-C$_4$-alkyl, C$_1$-C$_4$-alkoxy, CF$_3$, (C$_1$-C$_4$-alkoxy)carbonyl or nitro, R$^2$ is C$_1$-C$_4$-alkoxy which is unsubstituted or monosubstituted or polysubstituted by halogen or by (C$_1$-C$_4$-alkoxy)carbonyl, phenoxycarbonyl, benzyloxycarbonyl or phenyl, R$^3$ is H, C$_1$-C$_4$-alkyl or allyl, in particular H, R$^4$ is a radical of the formula

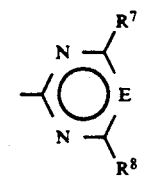

R$^7$ and R$^8$ independently of one another are halogen, C$_1$-C$_4$-alkyl, C$_1$-C$_4$-alkoxy or one of the last two abovementioned radicals which is halogenated, in particular the radicals CH$_3$, OCH$_3$, OC$_2$H$_5$, Cl, OCF$_2$H or CF$_3$, E is CH or N, and Z is O or S, preferably an oxygen atom.

The present invention furthermore relates to the process for the preparation of compounds of the general formula (I) or salts thereof, which comprises (a) reacting a compound of the formula (II)

R$^1$—Y—A—NR$^2$—SO$_2$—N=C=Z    (II)

with a compound of the formula (III)

H—NR$^3$R$^4$    (III)

where, in formulae (II) and (III), A, Y, Z, R$^1$, R$^2$, R$^3$ and R$^4$ are as defined in formula (I), or (b) reacting a compound of the formula (IV)

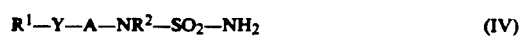

R$^1$—Y—A—NR$^2$—SO$_2$—NH$_2$    (IV)

with a carbamate, or thiocarbamate, of the formula (V)

where, in formulae (IV) and (V), R$^1$, R$^2$, R$^3$, R$^4$, A, Y and Z are as defined in formula (I) and R* is C$_1$-C$_6$-alkyl, C$_1$-C$_4$-haloalkyl, phenyl or a phenyl radical which is monosubstituted or polysubstituted by halogen, C$_1$-C$_4$-alkyl or nitro, or (c) reacting a carbamate, or thiocarbamate, of the formula (VI)

$$R^1-Y-A-NR^2-SO_2-NH-\underset{\underset{Z}{\|}}{C}-OR^* \quad (VI)$$

with a compound of the formula (III) mentioned under (a), where $R^1$, $R^2$, $R^*$, Y, A and Z are as defined, or (d) reacting a compound of the formula (VII) or (VIII)

$$R^1-Y-A-NH-R^2 \quad (VII)$$

$$R^1-Y-A-NH-R^2 \times HCl \quad (VIII)$$

with a compound of the formula (IX)

$$ClSO_2-NH-\underset{\underset{Z}{\|}}{C}-NR^3R^4 \quad (IX)$$

where, in formulae (VII) to (IX), A, Y, Z, $R^1$, $R^2$, $R^3$ and $R^4$ are as defined above.

The compounds of the formulae (II) and (III) are preferably reacted in aprotic solvents which are inert under the reaction conditions, such as, for example, acetonitrile, dichloromethane, toluene, tetrahydrofuran or dioxane, at temperatures of from 0° C to boiling point of the reaction mixture. The alkylsulfonyl isocyanates, or alkylsulfonyl isothiocyanates, of the formula (II) are novel and therefore likewise are the subject of the invention They can be prepared in a simple manner from the corresponding sulfonamides of the abovementioned formula (IV) analogously to customary procedures (cf., for example, EP-A 085,276). The compounds of the formula (II) can also be prepared from the compounds of the formula (VI) by reacting them with chlorosulfonyl isocyanate (cf., for example, DE-A 2,257,240).

The starting substances of the formula (III) are known or may be prepared by procedures known in principle, for example by cyclization of corresponding guanidine derivatives with appropriately substituted 1,3-diketones; cf., for example, "The chemistry of heterocyclic compounds" Vol. XVI (1962) and Supplement I (1970). It is also possible to form derivatives from cyanuric chloride; cf., for example, "The Chemistry of Heterocyclic Compounds" L. Rapaport: "s-Triazines and Derivatives" (1959).

The reaction of a compound (IV) with a heterocyclic carbamate of the formula (V) is preferably carried out in the presence of tertiary organic bases, for example 1,8-diazabicyclo-[5,4,0]-undec-7-ene (DBU), in inert solvents, such as acetonitrile or dioxane, at a temperature of from 20° C. to the boiling point of the reaction mixture; the process is analogous to the corresponding process from EP-A 44,807. The carbamates (V) required for this purpose are known from the literature or are prepared analogously to known processes or processes customary per se; a corresponding process is described in EP-A 70,804.

The carbamates of the formula (VI) are novel and likewise a subject of the invention They may be prepared by reacting the compounds of the formula (IV) with corresponding chloroformic esters (cf. EP-A 87,780). The reaction of the carbamates or thiocarbamates, of the formula (VI) with the aminoheterocycles of the formula (III) is preferably carried out in inert solvents, for example toluene, xylene, chlorobenzene, dioxane and acetonitrile, at a temperature of from 20° C. to the boiling point of the particular reaction mixture.

The compounds of the formulae (VII), (VIII) and (IX) may be prepared analogously to processes known from the literature or processes which are customary per se (cf. Chem. Ber. 96, 388 (1963); Z. Naturforsch. 36 b, 1673 (1981); J. Am. Chem. Soc. 87, 4359 (1965); Chem. Ber. 118, 564 (1985), U.S. Pat. No. 4,016,266 and J. Heterocycl. Chem. 8, 597 (1971)).

The sulfonylureas of the formula (I) which contain one or more asymmetric carbon atoms in the aliphatic radicals A, $R^1$ and $R^2$, are present in enantiomeric and-/or diastereomeric forms. In general, the corresponding compounds according to the invention are obtained as racemates or as mixtures of diastereomers. If desired, the customary techniques can be used for resolving these mixtures into the sterically uniform components. The compounds mentioned can also be obtained in pure form by using sterically uniform starting materials.

The formula (I) therefore embraces all abovementioned enantiomeric and diastereomeric forms of the compounds defined above.

The compounds of the formula I according to the invention have an excellent herbicidal activity against a broad range of economically important monocotyledon and dicotyledon harmful plants. The active substances also act efficiently on perennial weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be combated by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention likewise effect outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence on the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in plantings for agricultural use.

Moreover, the substances according to the invention have outstanding growth-regulating properties in crop plants. They engage in the metabolism of the plants in regulatory manner and can therefore be employed for the targeted influencing of plant constituents and for facilitating harvesting, for example, by triggering desiccation and stunted growth. In addition, they are also suitable for generally affecting and inhibiting undesired vegetative growth without simultaneously destroying the plants. Inhibition of vegetative growth is very important in many monocotyledon and dicotyledon crops, since lodging can be reduced or prevented completely by this means.

The compounds according to the invention can be employed in the form of wettable powders, emulsifiable concentrates, sprayable solutions, dusts or granules in the customary preparations.

Depending on the prevailing biological and/or physicochemical parameters, the compounds of the formula (I) can be formulated in many ways. The following possibilities are therefore suitable for formulation: wettable powders (WP), emulsifiable concentrates (EC), concentrated emulsions (EW), for example oil-in-water or water-in-oil emulsions, sprayable solutions or emulsions, dispersions on oil or water bases (SC), dusts (DP), seed-treatment agents, granules (G) such as soil granules or granules for scattering (FG), water-dispersible granules (WDG), ULV formulations, microcapsules or waxes.

These individual formulation types are known in principle and are described, for example, in: Winnacker-Küchler, "Chemische Technologie [Chemical Technology]", Volume 7, C. Hauser Verlag Munich, 4th Ed., 1986; van Valkenburg, "Pesticides Formulations", Marcel Dekker N Y, 2nd Ed. 1972-73; K. Martens, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H.v.Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp. Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" "[Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a ready mix or as a tank mix.

Wettable powders are preparations which are uniformly dispersible in water and which, besides the active substance, also contain wetting agents, for example polyoxyethylated alkylphenols, polyoxyethylated fatty alcohols, alkanesulfonates or alkylarylsulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example cyclohexanone, xylene and also higher-boiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products (for example block polymers, fatty alcohol/propylene oxide/ethylene oxide condensation products), sorbitan fatty acid esters, polyoxyethylene sorbitan fatty acid esters or polyoxethylene sorbitol esters.

Dusts can be obtained by grinding the active substance with finely divided solid substances, for example talc or natural clays, such as kaolin, bentonite, pyrophillite or diatomaceous earth. Granules, such as soil granules or granules for scattering or water-dispersible granules, can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

Disk granules, fluidized-bed granules, extruder granules and spray granules can be produced by customary methods; see, for example, the processes in "Spray-Drying Handbook" 3rd ed. 1979, G. Goodwin Ltd., London; J.E. Browning, "Agglomeration", Chemical and Engineering 1967, pages 147 et seq.; "Perry's Chemical Engineer's Handbook", 5th Ed., McGraw-Hill, New York 1973, p. 8-57.

For further information regarding the formulation of plant protection agents see, for example, G.C. Klingman, "Weed Control as a Science", John Wiley & Sons, Inc., New York, 1961, pages 81-96 and J.D. Freyer, S.A. Evans, "Weed Control Handbook", 5th Ed., Blackwell Scientific Publications, Oxford, 1968, pages 101-103.

The agrochemical preparations contain, as a rule, 0.1 to 99% by weight, in particular 0.1 to 95% by weight, of active substance of the formula (I).

The concentration of active substance in wettable powders is, for example, about 10 to 90% by weight, the remainder, to 100% by weight, is composed of conventional formulation components. In the case of emulsifiable concentrates, the concentration of active substance can be about 1 to 80, preferably 5 to 80, % by weight. Formulations in the form of dusts contain 1 to 30, usually preferably 5 to 20% by weight of active substance, sprayable solutions about 0.2 to 25, preferably 2 to 20, % by weight. In the case of water-dispersible granules, the active substance content depends partly on whether the active compound is liquid or solid and on which granulation auxiliaries, fillers etc. are used.

In general, the water-dispersible granules contain between 10 and 90% by weight of active substance.

In addition, the active substance formulations mentioned contain, if appropriate, the adhesives, wetting agents, dispersing agents, emulsifiers, penetrants, solvents, fillers or carriers which are conventional in each case. For use, the formulations, present in commercially available form, are diluted, if appropriate, in a customary manner, for example using water in the case of wettable powders, emulsifiable concentrates, dispersions and water-dispersible granules. Preparations in the form of dusts, soil granules or granules for scattering and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.005 and 10.0 kg/ha or more of active ingredient; preferably, however, it is between 0.01 and 5 kg/ha.

The examples which follow serve to illustrate the invention:

FORMULATION EXAMPLES a) A dust is obtained by mixing 10 parts by weight of a compound of the formula (I) and 90 parts by weight of talc as the inert substance and comminuting the mixture in a hammer mill.

b) A wettable powder which is readily dispersible in water is obtained by mixing 25 parts by weight of a compound of the formula (I), 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk-mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to above 277° C.), and grinding the mixture in a ball mill to a fineness of below 5 microns.

d) An emulsifiable concentrate is obtained from 15 parts by weight of a compound of the formula (I), 75 parts by weight of cyclohexane as the solvent and parts by weight of oxethylated nonylphenol as the emulsifier.

e) Water-dispersible granules are obtained by mixing 75 parts by weight of a compound of the formula

| 75 parts by weight | of a compound of the formula (I), |
|---|---|
| 10 parts by weight | of calcium ligninsulfonate, |
| 5 parts by weight | of sodium laurylsulfate, |
| 3 parts by weight | of polyvinyl alcohol and |
| 7 parts by weight | of kaolin. | grinding the mixture in a pinned disk mill, and granulating the powder in a fluidized bed by spraying on water a granulation liquid.

f) Alternatively, water-dispersible granules are obtained by homogenizing 25 parts by weight of a compound of the formula

| 25 parts by weight | of a compound of the formula (I), |
|---|---|
| 5 parts by weight | of sodium 2,2'-dinaphthyl-methane-6,6'-disulfonate, |
| 2 parts by weight | of sodium oleoylmethyltaurinate, |
| 1 parts by weight | of polyvinyl alcohol, |
| 17 parts by weight | of calcium carbonate and |
| 50 parts by weight | of water | in a colloidal mill and subjecting the mixture to precomminution, then grinding it in a bead mill and spraying the resulting suspension in a spray tower by means of a one-component nozzle, and drying it.

CHEMICAL EXAMPLES

A)

N-[(4,6-Dimethoxypyrimidin-2-yl)-aminocarbonyl]-N'-[2-(ethylsulfonyl)-ethyl]-N'-methoxyamino-sulfonamide (cf. Example 106, Table 1)

a) 2-Ethylsulfonyl-N-methoxyethylamine 8.2 g of sodium acetate are added to 8.5 g of O-methylhydroxylamine hydrochloride in 100 ml of methanol, and the mixture is stirred for 10 minutes. 9.6 g of vinylethyl sulfone are then added, and the mixture is heated for 2 hours at 50° C. It is then poured into ice-water and extracted with methylene chloride. The organic phase is evaporated on a rotary evaporator. This gives 11 g (82% of theory) of a crude product which can be further used without further purification.

b)

N-[(4,6-Dimethoxy-pyrimidin-2-yl)-aminocarbonyl]-N'-[2-(ethylsulfonyl)-ethyl]-N'-methoxyaminosulfonamide 3.82 g (0.027 mol) of chlorosulfonyl isocyanate are dissolved in 80 ml of $CH_2Cl_2$, and 4.19 g (0.027 mol) of 2-amino-4,6-dimethoxypyrimidine are added at $-70°$ C. After the mixture has been stirred for 1 hour at room temperature, a mixture of 4.5 g (0.027 mol) of 2-ethylsulfonyl-N-methoxyethylamine and 2.74 g (0.027 mol) of triethylamine in 50 ml of $CH_2Cl_2$ is added dropwise at $-70°$ C. The mixture is stirred for 18 hours at room temperature and extracted with water, the extract is dried with $MgSO_4$, and the product is precipitated with n-heptane. In this way, 8.65 g (75% of theory) of product with a melting point of 170°-172° C. are obtained.

B)

N-[(4,6-Dimethoxy-pyrimidin-2-yl)aminocarbonyl]-N'-[2-(dimethylaminosulfon-yl)-eth-1-yl]-N'-methoxyaminosulfonamide (cf. Example 273, Table 1)

a) 2-Dimethylaminosulfonyl-N-methoxy-ethylamine 12.37 g (0.148 mol) of O-methylhydroxylamine hydrochloride are dissolved in 120 ml of methanol, and the solution together with 12.1 g (0.148 mol) of sodium acetate is stirred at room temperature for 10 minutes. 15.96 g (0.118 mol) of N-dimethyl-vinylsulfonamide (prepared analogously to Synthesis 1983, p. 816)—dissolved in 30 ml of methanol—are then added dropwise. After the suspension has been stirred for 15 hours at room temperature and for 3 hours at 50° C., it is poured into ice-water, the mixture is extracted several times with $CH_2Cl_2$, and the organic extract is dried over Na$_2$SO$_2$. 15.8 g (69.9% of theory) of a yellowish oil which can be employed without further purification are obtained.

b) N-[(4,6-Dimethoxy-pyrimidin-2-yl)aminocarbonyl]-N'-[2-(dimethylaminosulfonyl)-eth-1-yl]-N'-methoxyaminosulfonamide 4.19 g (0.027 mol) of 2-amino-4,6-dimethoxypyrimidine were added to 3.82 g (0.027 mol) of chlorosulfonyl isocyanate in 50 ml of CH$_2$Cl$_2$, at −70° C. After the mixture has been stirred for 1 hour at room temperature, a mixture of 4.92 g (0.027 mol) of 2-dimethylaminosulfonyl-N-methoxyethylamine and 2.74 g (0.027 mol) of triethylamine in 50 ml of CH$_2$Cl$_2$ is added dropwise at −70° C. Stirring is continued for 18 hours at room temperature, the mixture is extracted with water, the extract is dried over sodium sulfate, and the product is precipitated with n-heptane. 8.69 g (72.9% of theory) of product of melting point 178°–180° C. are obtained.

The compounds defined in Table 1 below are obtained in an analogous manner.

TABLE 1

$$R^1-Y-A-\underset{R^3}{\overset{R^2}{N}}-SO_2-NH-\overset{O}{\underset{\|}{C}}-N\text{-pyrimidine ring with }R^7, R^8, E$$

| Ex. No. | A | —Y—R$^1$ | R$^2$ | R$^3$ | R$^7$ | R$^8$ | E | M.p. (°C.) |
|---|---|---|---|---|---|---|---|---|
| 1 | —CH$_2$CH$_2$— | —S—C$_6$H$_5$ | —OC$_2$H$_5$ | H | CH$_3$ | CH$_3$ | CH | |
| 2 | " | " | " | H | OCH$_3$ | CH$_3$ | " | |
| 3 | " | " | " | H | OCH$_3$ | OCH$_3$ | " | |
| 4 | " | " | " | H | " | Cl | " | |
| 5 | " | " | " | H | OCHF$_2$ | CH$_3$ | " | |
| 6 | " | " | " | H | " | CF$_3$ | " | |
| 7 | " | " | " | H | " | OCHF$_2$ | " | |
| 8 | " | " | " | H | CH$_3$ | Cl | " | |
| 9 | " | " | " | H | OCH$_3$ | BR | " | |
| 10 | " | " | " | H | " | NHCH$_3$ | " | |
| 11 | " | " | " | H | OCHF$_2$ | OCH$_3$ | " | |
| 12 | " | —SO$_2$—C$_6$H$_5$ | " | H | CH$_3$ | CH$_3$ | " | |
| 13 | " | " | " | H | OCH$_3$ | CH$_3$ | " | |
| 14 | " | " | " | H | " | OCH$_3$ | " | |
| 15 | " | " | " | H | " | Cl | " | |
| 16 | " | " | " | H | OCHF$_2$ | CH$_3$ | " | |
| 17 | " | " | " | H | " | CF$_3$ | " | |
| 18 | " | " | " | H | " | OCHF$_2$ | " | |
| 19 | " | " | " | H | CH$_3$ | Cl | " | |
| 20 | " | " | " | H | OCH$_3$ | Br | " | |
| 21 | " | —SO$_2$—CH(CH$_3$)$_2$ | OCH$_3$ | H | OCH$_3$ | NHCH$_3$ | " | |
| 22 | " | " | " | H | OCHF$_2$ | OCH$_3$ | " | |
| 23 | " | " | " | H | CH$_3$ | CH$_3$ | " | |
| 24 | " | " | " | H | OCH$_3$ | CH$_3$ | " | 134 |
| 25 | " | " | " | H | " | OCH$_3$ | " | 184–185 |
| 26 | " | " | " | H | " | Cl | " | 193 |
| 27 | " | " | " | H | OCHF$_2$ | CH$_3$ | " | |
| 28 | —CH$_2$CH$_2$— | —SO$_2$—CH(CH$_3$)$_2$ | —OCH$_3$ | H | OCHF$_2$ | CF$_3$ | CH | |
| 29 | " | " | " | H | " | OCHF$_2$ | CH | |
| 30 | " | " | " | H | CH$_3$ | Cl | CH | 62 |
| 31 | " | " | " | H | OCH$_3$ | Br | CH | |
| 32 | " | " | " | H | " | NHCH$_3$ | N | |
| 33 | " | " | " | H | " | OCH$_3$ | N | 159 |
| 34 | " | —S—C$_2$H$_5$ | " | H | CH$_3$ | CH$_3$ | CH | |
| 35 | " | " | " | H | OCH$_3$ | CH$_3$ | " | |
| 36 | " | " | " | H | " | OCH$_3$ | " | |
| 37 | " | " | " | H | " | Cl | " | |
| 38 | " | " | " | H | OCHF$_2$ | CH$_3$ | " | |
| 39 | " | " | " | H | " | CF$_3$ | " | |
| 40 | " | " | " | H | " | OCHF$_2$ | " | |
| 41 | " | " | " | H | CH$_3$ | Cl | " | |
| 42 | " | " | " | H | OCH$_3$ | Br | " | |
| 43 | " | " | " | H | " | NHCH$_3$ | " | |
| 44 | " | " | " | H | OCHF$_2$ | OCH$_3$ | " | |
| 45 | " | —SO$_2$—C$_6$H$_{11}$ | " | H | OCH$_3$ | OCH$_3$ | N | |
| 46 | " | " | " | H | OCHF$_2$ | OCHF$_2$ | N | |
| 47 | " | " | " | H | CH$_3$ | CH$_3$ | N | |
| 48 | " | —SC$_6$H$_{11}$ | " | H | OCH$_3$ | OCH$_3$ | N | |
| 49 | " | " | " | H | CH$_3$ | OCHF$_2$ | N | |
| 50 | " | —S—CH$_2$—C$_6$H$_5$ | " | H | CH$_3$ | CH$_3$ | CH | |
| 51 | " | " | " | H | OCH$_3$ | CH$_3$ | " | |
| 52 | " | " | " | H | OCH$_3$ | OCH$_3$ | " | |
| 53 | " | " | " | H | OCH$_3$ | Cl | " | |
| 54 | " | " | " | H | OCHF$_2$ | CH$_3$ | " | |
| 55 | " | " | " | H | OCHF$_2$ | CF$_3$ | " | |
| 56 | " | " | " | H | OCHF$_2$ | OCHF$_2$ | " | |
| 57 | —CH$_2$CH$_2$— | —S—CH$_2$C$_6$H$_5$ | —OCH$_3$ | H | CH$_3$ | Cl | CH | |

TABLE 1-continued $$R^1-Y-A-\underset{R^3}{\underset{|}{N}}-SO_2-NH-\underset{}{\overset{O}{\overset{\|}{C}}}-\underset{R^3}{\underset{|}{N}}\underset{N}{\overset{N}{\diagdown}}\underset{R^8}{\overset{R^7}{\diagup}}E$$

| Ex. No. | A | —Y—R¹ | R² | R³ | R⁷ | R⁸ | E | M.p. (°C.) |
|---|---|---|---|---|---|---|---|---|
| 58 | " | " | " | H | OCH₃ | Br | " | |
| 59 | " | " | " | H | OCH₃ | NHCH₃ | " | |
| 60 | " | " | " | H | OCHF₂ | OCH₃ | " | |
| 61 | " | " | —OCH(CH₃)₂ | H | CH₃ | CH₃ | " | |
| 62 | " | " | " | H | OCH₃ | CH₃ | " | |
| 63 | " | " | " | H | OCH₃ | OCH₃ | " | |
| 64 | " | " | " | H | OCH₃ | Cl | " | |
| 65 | " | " | " | H | OCHF₂ | CH₃ | " | |
| 66 | " | " | " | H | " | CF₃ | " | |
| 67 | " | " | " | H | " | OCHF₂ | " | |
| 68 | " | " | " | H | CH₃ | Cl | " | |
| 69 | " | " | " | H | OCH₃ | Br | " | |
| 70 | " | " | " | H | OCH₃ | NHCH₃ | " | |
| 71 | " | " | " | H | OCHF₂ | OCH₃ | " | |
| 72 | " | —SO₂—CH₃ | —OCH₃ | CH₃ | OCH₃ | OCH₃ | N | |
| 73 | " | " | " | " | CH₃ | OCHF₂ | " | |
| 74 | " | " | " | H | OCH₃ | OCH₃ | " | 158 |
| 75 | " | " | " | CH₃ | OCH₃ | CF₃ | " | |
| 76 | " | —SO₂—CH₂C₆H₅ | " | H | CH₃ | CH₃ | " | |
| 77 | " | " | " | " | OCH₃ | CH₃ | " | |
| 78 | " | " | " | " | OCH₃ | OCH₃ | " | |
| 79 | " | " | " | " | OCH₃ | Cl | " | |
| 80 | " | " | " | " | OCHF₂ | CH₃ | " | |
| 81 | " | " | " | " | OCHF₂ | CF₃ | " | |
| 82 | " | " | " | " | OCHF₂ | OCHF₂ | " | |
| 83 | " | " | " | " | CH₃ | Cl | " | |
| 84 | " | " | " | " | OCH₃ | Br | " | |
| 85 | " | " | " | " | OCH₃ | NHCH₃ | " | |
| 86 | —CH₂CH₂— | —SO₂CH₂C₆H₅ | —OCH₃ | H | OCHF₂ | OCH₃ | N | |
| 87 | " | —S—CH₃ | —OC₂H₅ | H | CH₃ | CH₃ | " | |
| 88 | " | " | " | " | OCH₃ | CH₃ | " | |
| 89 | " | " | " | " | OCH₃ | OCH₃ | " | |
| 90 | " | " | " | " | OCH₃ | Cl | " | |
| 91 | " | " | " | " | OCHF₂ | CH₃ | " | |
| 92 | " | " | " | " | OCHF₂ | CF₃ | " | |
| 93 | " | " | " | " | OCHF₂ | OCHF₂ | " | |
| 94 | " | " | " | " | CH₃ | Cl | " | |
| 95 | " | " | " | " | OCH₃ | Br | " | |
| 96 | " | " | " | " | OCH₃ | NHCH₃ | " | |
| 97 | " | " | " | " | OCHF₂ | OCH₃ | " | |
| 98 | " | —SO₂C₂H₅ | —OCH(CH₃)₂ | " | OCHF₂ | CF₃ | CH | |
| 99 | " | " | " | " | OCHF₂ | OCHF₂ | " | |
| 100 | " | " | " | " | CH₃ | Cl | " | |
| 101 | " | " | " | " | OCH₃ | Br | " | |
| 102 | " | " | " | " | OCH₃ | NHCH₃ | " | |
| 103 | " | " | " | " | OCHF₂ | OCH₃ | " | |
| 104 | " | " | —OCH₃ | H | CH₃ | CH₃ | " | |
| 105 | " | " | " | " | OCH₃ | CH₃ | " | 138 |
| 106 | " | " | " | " | OCH₃ | OCH₃ | " | 170–172 |
| 107 | " | " | " | " | OCH₃ | Cl | " | 172 |
| 108 | " | " | —OCH₂CH₂CH₃ | " | CH₃ | CH₃ | " | |
| 109 | " | " | " | " | OCH₃ | CH₃ | " | |
| 110 | " | " | " | " | OCH₃ | OCH₃ | " | |
| 111 | " | " | " | " | OCH₃ | Cl | " | |
| 112 | " | " | " | " | OCHF₂ | CH₃ | " | |
| 113 | " | " | " | " | OCHF₂ | CF₃ | " | |
| 114 | " | " | " | " | OCHF₂ | OCHF₂ | " | |
| 115 | —CH₂CH₂— | —SO₂C₂H₅ | —OCH₂CH₂CH₃ | H | CH₃ | Cl | CH | |
| 116 | " | " | " | " | OCH₃ | Br | " | |
| 117 | " | " | " | " | OCH₃ | NHCH₃ | " | |
| 118 | " | " | " | " | OCHF₂ | OCH₃ | " | |
| 119 | " | " | —OCH(CH₃)₂ | " | CH₃ | CH₃ | " | |
| 120 | " | " | " | " | OCH₃ | CH₃ | " | |
| 121 | " | " | " | " | OCH₃ | OCH₃ | " | |
| 122 | " | " | " | " | OCH₃ | Cl | " | |
| 123 | " | " | " | " | OCHF₂ | CH₃ | " | |
| 124 | " | " | —O(CH₂)₃CH₃ | " | OCH₃ | NHCH₃ | " | |
| 125 | " | " | " | " | OCHF₂ | OCH₃ | " | |
| 126 | " | " | —OCH₃ | " | OCHF₂ | CH₃ | " | |
| 127 | " | " | " | " | " | CF₃ | " | |
| 128 | " | " | " | " | " | OCHF₂ | " | |

TABLE 1-continued

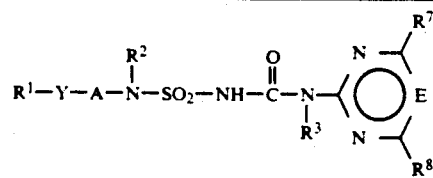

| Ex. No. | A | —Y—R¹ | R² | R³ | R⁷ | R⁸ | E | M.p. (°C.) |
|---|---|---|---|---|---|---|---|---|
| 129 | " | " | " | " | $CH_3$ | Cl | " | 59-62 |
| 130 | " | " | " | " | $OCH_3$ | Br | " | |
| 131 | " | " | " | " | $OCH_3$ | $NHCH_3$ | " | |
| 132 | " | " | " | " | $OCHF_2$ | $OCH_3$ | " | |
| 133 | " | " | —O(CH₂)₃CH₃ | " | $CH_3$ | $CH_3$ | " | |
| 134 | " | " | " | " | $OCH_3$ | $CH_3$ | " | |
| 135 | " | " | " | " | $OCH_3$ | $OCH_3$ | " | |
| 136 | " | " | " | " | $OCH_3$ | Cl | " | |
| 137 | " | " | " | " | $OCHF_2$ | $CH_3$ | " | |
| 138 | " | " | " | " | $OCHF_2$ | $CF_3$ | " | |
| 139 | " | " | " | " | $OCHF_2$ | $OCHF_2$ | " | |
| 140 | " | " | " | " | $CH_3$ | Cl | " | |
| 141 | " | " | " | " | $OCH_3$ | Br | " | |
| 142 | " | " | —OC₆H₁₁ | " | $CH_3$ | $CH_3$ | " | |
| 143 | " | " | " | " | $OCH_3$ | $CH_3$ | " | |
| 144 | " | " | " | " | $OCH_3$ | $OCH_3$ | " | |
| 145 | —CH₂CH₂— | —SO₂C₂H₅ | —OC₆H₁₁ | H | $OCH_3$ | Cl | CH | |
| 146 | " | " | " | " | $OCHF_2$ | $CH_3$ | " | |
| 147 | " | " | " | " | $OCHF_2$ | $CF_3$ | " | |
| 148 | " | " | " | " | $OCHF_2$ | $OCHF_2$ | " | |
| 149 | " | " | " | " | $CH_3$ | Cl | " | |
| 150 | " | " | " | " | $OCH_3$ | Br | " | |
| 151 | " | " | " | " | $OCH_3$ | $NHCH_3$ | " | |
| 152 | " | " | " | " | $OCHF_2$ | $OCH_3$ | " | |
| 153 | " | —SO₂CH₃ | —OC₃H₇ | " | $CH_3$ | $CH_3$ | " | |
| 154 | " | " | " | " | $OCH_3$ | $CH_3$ | " | |
| 155 | " | " | " | " | " | $OCH_3$ | " | |
| 156 | " | " | " | " | " | Cl | " | |
| 157 | " | " | " | " | $OCHF_2$ | $CH_3$ | " | |
| 158 | " | " | " | " | $OCHF_2$ | $CF_3$ | " | |
| 159 | " | " | " | " | $OCHF_2$ | $OCHF_2$ | " | |
| 160 | " | " | " | " | $CH_3$ | Cl | " | |
| 161 | " | " | " | " | $OCH_3$ | Br | " | |
| 162 | " | " | " | " | $OCH_3$ | $NHCH_3$ | " | |
| 163 | " | " | " | " | $OCHF_2$ | $OCH_3$ | " | |
| 164 | " | " | —OCH₂CH₃ | " | $CH_3$ | $CH_3$ | " | |
| 165 | " | " | " | " | $OCH_3$ | $CH_3$ | " | 145-147 |
| 166 | " | " | " | " | " | $OCH_3$ | " | 160-163 |
| 167 | " | " | " | " | " | Cl | " | 178 |
| 168 | " | " | " | " | $OCHF_2$ | $CH_3$ | " | |
| 169 | " | " | " | " | " | $CF_3$ | " | |
| 170 | " | " | " | " | " | $OCHF_2$ | " | |
| 171 | " | " | " | " | $CH_3$ | Cl | " | 50-51 |
| 172 | " | " | " | " | $OCH_3$ | Br | " | |
| 173 | " | " | " | " | $OCH_3$ | $NHCH_3$ | " | |
| 174 | " | " | " | " | $OCHF_2$ | $OCH_3$ | " | |
| 175 | —CH₂CH₂— | —SO₂CH₂CH₃ | —OC₆H₅ | H | $CH_3$ | $CH_3$ | CH | |
| 176 | " | " | " | " | $CH_3$ | $OCH_3$ | " | |
| 177 | " | " | " | " | $OCH_3$ | $OCH_3$ | " | |
| 178 | " | " | " | " | $OCH_3$ | $OCH_3$ | N | |
| 179 | " | " | " | " | $CH_3$ | $OCH_3$ | N | |
| 180 | " | " | " | " | $OCHF_2$ | $OCHF_2$ | CH | |
| 181 | " | —SO₂C₆H₅ | —O—CH₃ | " | $CH_3$ | $CH_3$ | " | |
| 182 | " | " | " | " | $CH_3$ | $OCH_3$ | " | |
| 183 | " | " | " | " | $OCH_3$ | $OCH_3$ | " | |
| 184 | " | " | " | " | $OCH_3$ | $OCH_3$ | N | |
| 185 | " | " | " | " | $CH_3$ | $OCH_3$ | N | |
| 186 | " | " | " | " | $OCHF_2$ | $OCH_3$ | CH | |
| 187 | " | —SO₂N(CH₃)₂ | " | " | $CH_3$ | $CH_3$ | " | 145-147 |
| 188 | " | " | " | " | $CH_3$ | $OCH_3$ | " | 162-164 |
| 189 | " | " | " | " | $OCH_3$ | Cl | " | 168-171 |
| 190 | " | " | " | " | $OCH_3$ | $OCH_3$ | N | 124 |
| 191 | " | " | " | " | $CH_3$ | $OCH_3$ | N | 112-113 |
| 192 | " | " | " | " | $OCHF_2$ | $OCHF_2$ | CH | 88-89 |
| 193 | " | " | —OC₂H₅ | " | $CH_3$ | $CH_3$ | " | |
| 194 | " | " | " | " | $CH_3$ | $OCH_3$ | " | |
| 195 | " | " | " | " | $OCH_3$ | $OCH_3$ | " | |
| 196 | " | " | " | " | $OCH_3$ | $OCH_3$ | N | |
| 197 | " | " | " | " | $CH_3$ | $OCH_3$ | N | |
| 198 | " | " | " | " | $OCHF_2$ | $OCHF_2$ | CH | |
| 199 | " | " | —OC₃H₇(n) | " | $OCH_3$ | $OCH_3$ | " | |

5,129,941

TABLE 1-continued $$R^1-Y-A-\underset{R^2}{N}-SO_2-NH-\underset{}{\overset{O}{C}}-\underset{R^3}{N}-\text{[pyrimidine/triazine ring with } R^7, R^8, E\text{]}$$

| Ex. No. | A | —Y—R¹ | R² | R³ | R⁷ | R⁸ | E | M.p. (°C.) |
|---|---|---|---|---|---|---|---|---|
| 200 | " | " | " | " | OCH₃ | OCH₃ | N | |
| 201 | " | " | " | " | CH₃ | OCH₃ | CH | |
| 202 | " | " | " | " | CH₃ | OCH₃ | N | |
| 203 | " | " | —OC₄H₉(n) | " | OCH₃ | OCH₃ | CH | |
| 204 | " | " | " | " | OCH₃ | Cl | " | |
| 205 | —CH₂CH₂— | —SO₂NHCH₃ | OCH₃ | H | OCH₃ | OCH₃ | CH | |
| 206 | " | " | " | " | OCH₃ | Cl | " | |
| 207 | " | " | " | " | OCH₃ | CH₃ | " | |
| 208 | " | " | " | " | CH₃ | CH₃ | " | |
| 209 | " | " | " | " | CH₃ | OCH₃ | N | |
| 210 | " | " | " | " | OCH₃ | OCH₃ | N | |
| 211 | " | —SO₂NHC₂H₅ | " | " | OCH₃ | OCH₃ | CH | |
| 212 | " | " | " | " | OCH₃ | Cl | " | |
| 213 | " | " | " | " | OCH₃ | CH₃ | N | |
| 214 | " | " | " | " | OCH₃ | OCH₃ | N | |
| 215 | " | —SO₂N(pyrrolidine) | " | " | OCH₃ | OCH₃ | CH | |
| 216 | " | " | " | CH₃ | OCH₃ | OCH₃ | " | |
| 217 | " | " | " | H | OCH₃ | CH₃ | " | |
| 218 | " | —SO₂N(piperidine) | " | " | OCH₃ | CH₃ | " | |
| 219 | " | " | " | " | OCH₃ | OCH₃ | " | |
| 220 | " | —SO₂C₂H₅ | " | CH₃ | OCH₃ | OCH₃ | " | |
| 221 | " | " | " | CH₃ | OCH₃ | CH₃ | " | |
| 222 | " | —SO₂—N(CH₃)₂ | " | CH₃ | OCH₃ | OCH₃ | CH | |
| 223 | " | " | " | CH₃ | OCH₃ | CH₃ | N | |
| 224 | " | —SO₂NHCH₃ | " | CH₃ | OCH₃ | OCH₃ | CH | |
| 225 | " | —SO₂CH(CH₃)₂ | OC₂H₅ | H | OCH₃ | OCH₃ | CH | 175 |
| 226 | " | " | " | " | OCH₃ | CH₃ | CH | 50 |
| 227 | " | " | " | " | Cl | CH₃ | CH | 56–60 |
| 228 | " | " | " | " | OCH₃ | OCH₃ | N | 162 |
| 229 | —CH₂CH₂— | —SO₂C₂H₅ | OCH₃ | H | Cl | CH₃ | CH | 59–62 |
| 230 | " | " | " | " | OCH₃ | OCH₃ | N | 176–178 |
| 231 | " | " | OC₂H₅ | " | " | " | CH | 180–182 |
| 232 | " | " | " | " | " | CH₃ | CH | 51–53 |
| 233 | " | " | " | " | Cl | CH₃ | CH | 55–60 |
| 234 | " | " | " | " | OCH₃ | OCH₃ | N | 172–174 |
| 235 | " | " | " | " | OCHF₂ | OCHF₂ | CH | |
| 236 | " | " | " | " | " | CH₃ | CH | |
| 237 | CH₂CH₂ | SO₂CH₃ | OCH₃ | H | OCH₃ | OCH₃ | CH | 184 |
| 238 | " | " | " | " | " | CH₃ | " | 152–153 |
| 239 | " | " | " | " | Cl | " | " | 49–50 |
| 240 | " | " | OC₂H₅ | " | OCH₃ | OCH₃ | N | 155–156 |
| 241 | —CH₂CH₂— | —SO₂(n)—C₃H₇ | OCH₃ | H | CH₃ | CH₃ | CH | 129 |
| 242 | " | " | " | " | OCH₃ | CH₃ | CH | 160 |
| 243 | " | " | " | " | OCH₃ | CH₃ | CH | |
| 244 | " | " | " | " | OCH₃ | OCH₃ | N | |
| 245 | " | " | OC₂H₅ | " | OCH₃ | OCH₃ | CH | |
| 246 | " | " | " | " | OCH₃ | OCH₃ | N | |
| 247 | " | " | " | " | OCH₃ | CH₃ | CH | |
| 248 | " | " | " | " | CH₃ | CH₃ | CH | |
| 249 | " | —SO₂C₆H₅ | OCH₃ | " | OCH₃ | OCH₃ | CH | |
| 250 | " | " | " | " | OCH₃ | OCH₃ | N | |
| 251 | " | " | " | " | OCH₃ | CH₃ | CH | |
| 252 | " | " | " | " | CH₃ | CH₃ | CH | |
| 253 | " | " | OC₂H₅ | " | OCH₃ | OCH₃ | CH | |
| 254 | " | " | " | " | OCH₃ | OCH₃ | N | |
| 255 | " | " | " | " | OCH₃ | CH₃ | CH | |
| 256 | " | " | " | " | CH₃ | CH₃ | CH | |
| 257 | —CH₂CH₂— | —SOC₂H₅ | OCH₃ | H | OCH₃ | OCH₃ | CH | |
| 258 | " | " | " | " | OCH₃ | OCH₃ | N | |

TABLE 1-continued

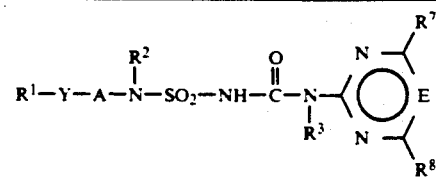

| Ex. No. | A | —Y—R¹ | R² | R³ | R⁷ | R⁸ | E | M.p. (°C.) |
|---|---|---|---|---|---|---|---|---|
| 259 | " | " | " | " | OCH₃ | CH₃ | CH | |
| 260 | " | " | " | " | CH₃ | CH₃ | CH | |
| 261 | " | " | OC₂H₅ | " | OCH₃ | OCH₃ | CH | |
| 262 | " | " | " | " | OCH₃ | OCH₃ | N | |
| 263 | " | " | " | " | OCH₃ | CH₃ | CH | |
| 264 | " | " | " | " | CH₃ | CH₃ | CH | |
| 265 | " | —SOCH₃ | OCH₃ | " | OCH₃ | OCH₃ | CH | |
| 266 | " | " | " | " | OCH₃ | OCH₃ | N | |
| 267 | " | " | " | " | OCH₃ | CH₃ | CH | |
| 268 | " | " | " | " | CH₃ | CH₃ | CH | |
| 269 | " | " | OC₂H₅ | " | OCH₃ | OCH₃ | CH | |
| 270 | " | " | " | " | OCH₃ | OCH₃ | N | |
| 271 | " | " | " | " | OCH₃ | CH₃ | CH | |
| 272 | " | " | " | " | CH₃ | CH₃ | CH | |
| 273 | " | —SO₂N(CH₃)₂ | OCH₃ | " | OCH₃ | OCH₃ | CH | 178-180 |
| 275 | " | —SO₂N(C₂H₅)₂ | " | " | OCH₃ | OCH₃ | CH | |
| 276 | " | " | " | " | CH₃ | CH₃ | CH | |
| 277 | " | " | " | " | OCH₃ | CH₃ | CH | |
| 278 | " | " | " | " | OCH₃ | OCH₃ | N | |
| 279 | " | " | OC₂H₅ | " | OCH₃ | OCH₃ | CH | |
| 280 | " | " | OC₆H₅ | " | OCH₃ | OCH₃ | CH | |
| 281 | " | " | " | " | OCH₃ | Cl | CH | |
| 282 | " | —SO₂N(C₃H₇)₂ | OCH₃ | " | OCH₃ | OCH₃ | CH | |
| 283 | " | —SO₂NH(n-C₄H₉) | OCH₃ | " | OCH₃ | OCH₃ | CH | |
| 284 | " | —SO₂—NH—OCH₃ | OCH₃ | " | OCH₃ | OCH₃ | CH | |
| 285 | " | —SO₂—NH—OC₂H₅ | OCH₃ | " | OCH₃ | OCH₃ | CH | |
| 286 | " | —SO₂N(OCH₃)(CH₃) | OCH₃ | " | OCH₃ | OCH₃ | CH | |
| 287 | CH₂CH₂CH₂ | —SO₂C₂H₅ | OCH₃ | H | OCH₃ | OCH₃ | CH | |
| 288 | " | " | OCH₃ | " | CH₃ | CH₃ | CH | |
| 289 | " | " | OCH₃ | " | OCH₃ | CH₃ | CH | |
| 290 | " | " | OCH₃ | " | OCH₃ | Cl | CH | |
| 291 | " | " | OCH₃ | CH₃ | OCH₃ | OCH₃ | CH | |
| 292 | " | " | OCH₃ | CH₃ | OCH₃ | OCH₃ | N | |
| 293 | " | —SO₂N(CH₃)₂ | OCH₃ | H | OCH₃ | OCH₃ | CH | |
| 294 | " | " | OCH₃ | H | CH₃ | CH₃ | CH | |
| 295 | —CH₂CH₂CH₂CH₂— | SO₂CH₃ | " | H | OCH₃ | OCH₃ | CH | |
| 296 | —CH₂— | " | " | H | OCH₃ | OCH₃ | CH | |
| 297 | —CH(CH₃)— | " | " | H | OCH₃ | OCH₃ | CH | |
| 298 | —CH₂CH(CH₃)— | SO₂C₂H₅ | " | H | OCH₃ | OCH₃ | CH | |
| 299 | —C(CH₃)₂— | " | " | H | CH₃ | CH₃ | CH | |
| 300 | " | " | " | H | OCH₃ | OCH₃ | CH | |

N-[(4,6-Dimethoxy-pyrimidin-2-yl)-aminocarbonyl]-N'-(methylsulfonyl)-N'-(methoxy)aminosulfonamide (cf. Ex. 473, Table 2)

a) N-Methylsulfonyl-methoxyamino-sulfonyl isocyanate 3.4 g (0.0272 mol) of O-methyl-N-methylsulfonylhydroxylamine (prepared in accordance with Z. Naturforsch. 36b, 1673 (1981)) are suspended in 80 ml of anhydrous chlorobenzene, and 2.53 ml (4.10 g; 0.029 mol) of chlorosulfonyl isocyanate are added at 0° C. The reaction mixture is then heated slowly while nitrogen is passed through, during which process the suspension changes into a clear solution at 40° C. After the mixture has been refluxed for about 3 hours, it is cooled and evaporated in a rotary evaporator, and the residue is dried under a high vacuum. 6.18 g (99% of theory) of N-methylsulfonyl-methoxyamino-sulfonyl isocyanate which can be employed in the next step without further purification are obtained.

b) N-[(4,6-Dimethoxy-pyrimidin-2-yl)aminocarbonyl]-N'-(methylsulfonyl)-N'-(methoxy)-aminosulfonamide 4.16 g (0.0268 mol) of 2-amino-4,6-dimethoxypyrimidine are dissolved in 100 ml of anhydrous dichloromethane, and 6.17 g (0.0268 mol) of N-methylsulfonyl-methoxyamino-sulfonyl isocyanate are added at 0° C. After the mixture has been stirred for 18 hours at room temperature, it is refluxed for 2 hours and then extracted with 0.5N hydrochloric acid. After the extract has been dried over sodium sulfate, the product is precipitated at 0° C. using n-heptane. 10.02 g (97.1% of theory) of N-[(4,6-dimethoxy-pyrimidin-2-yl)aminocarbonyl]-N'-(methylsulfonyl)-N'-(methoxy)-aminosulfonamide of melting point 142°-144° C. are obtained.

The remaining sulfonylureas of the general formula (I) according to the invention which are listed in Table 2 below are prepared in the same manner, A denoting a direct bond.

TABLE 2

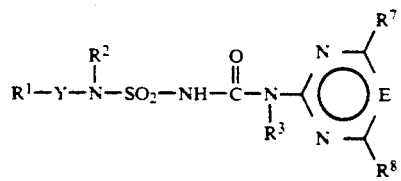

| Ex. No. | —Y—R¹ | R² | R³ | R⁷ | R⁸ | E | M.p. (°C.) |
|---|---|---|---|---|---|---|---|
| 301 | —SO₂—C₆H₅ | OC₂H₅ | H | CH₃ | CH₃ | CH | |
| 302 | " | " | H | OCH₃ | CH₃ | CH | |
| 303 | " | " | H | OCH₃ | OCH₃ | CH | |
| 304 | " | " | H | OCH₃ | Cl | CH | |
| 305 | " | " | H | OCHF₂ | CH₃ | CH | |
| 306 | " | " | H | OCHF₂ | CF₃ | CH | |
| 307 | " | " | H | OCHF₂ | OCHF₂ | CH | |
| 308 | " | " | H | CH₃ | Cl | CH | |
| 309 | " | " | H | OCH₃ | Br | CH | |
| 310 | SO₂—CH(CH₃)₂ | OCH₃ | H | OCH₃ | NHCH₃ | CH | |
| 311 | " | " | H | OCHF₂ | OCH₃ | CH | |
| 312 | " | " | H | CH₃ | CH₃ | CH | |
| 313 | " | " | H | OCH₃ | CH₃ | CH | |
| 314 | " | " | H | OCH₃ | OCH₃ | CH | 132–133 |
| 315 | " | " | H | OCH₃ | Cl | CH | |
| 316 | " | " | H | OCHF₂ | CH₃ | CH | |
| 317 | " | " | H | OCHF₂ | CF₃ | CH | |
| 318 | " | " | H | OCHF₂ | OCHF₂ | CH | |
| 319 | " | " | H | CH₃ | Cl | CH | |
| 320 | " | " | H | OCH₃ | Br | CH | |
| 321 | " | " | H | OCH₃ | NHCH₃ | N | |
| 322 | " | " | H | OCH₃ | OCH₃ | N | |
| 323 | —SO₂—C₆H₁₁ | " | H | OCH₃ | OCH₃ | N | |
| 324 | " | " | H | OCHF₂ | OCHF₂ | N | |
| 325 | " | " | H | CH₃ | CH₃ | N | |
| 326 | —SO₂—CH₃ | OCH₃ | CH₃ | OCH₃ | OCH₃ | N | |
| 327 | " | " | CH₃ | CH₃ | OCHF₂ | N | |
| 328 | " | " | H | OCH₃ | OCH₃ | N | |
| 329 | " | " | CH₃ | OCH₃ | CF₃ | N | |
| 330 | SO₂—CH₂C₆H₅ | " | H | CH₃ | CH₃ | N | |
| 331 | " | " | H | OCH₃ | CH₃ | N | |
| 332 | " | " | H | OCH₃ | OCH₃ | N | |
| 333 | " | " | H | OCH₃ | Cl | N | |
| 334 | " | " | H | OCHF₂ | CH₃ | N | |
| 335 | " | " | H | OCHF₂ | CF₃ | N | |
| 336 | " | " | H | OCHF₂ | OCHF₂ | N | |
| 337 | " | " | H | CH₃ | Cl | N | |
| 338 | " | " | H | OCH₃ | Br | N | |
| 339 | " | " | H | OCH₃ | NHCH₃ | N | |
| 340 | SO₂—C₂H₅ | OCH(CH₃)₂ | H | OCHF₂ | CF₃ | CH | |
| 341 | " | " | H | OCHF₂ | OCHF₂ | CH | |
| 342 | " | " | H | CH₃ | Cl | CH | |
| 343 | " | " | H | OCH₃ | Br | CH | |
| 344 | " | " | H | OCH₃ | NHCH₃ | CH | |
| 345 | " | " | H | OCHF₂ | OCH₃ | CH | |
| 346 | " | OCH₃ | H | CH₃ | CH₃ | CH | |
| 347 | " | " | H | OCH₃ | CH₃ | CH | 85–90 |
| 348 | " | " | H | OCH₃ | OCH₃ | CH | 159–160 |
| 349 | " | " | H | OCH₃ | Cl | CH | |
| 350 | " | OCH₂CH₂CH₃ | H | CH₃ | CH₃ | CH | |
| 351 | " | " | H | OCH₃ | CH₃ | CH | |
| 352 | " | " | H | OCH₃ | OCH₃ | CH | |
| 353 | " | " | H | OCH₃ | Cl | CH | |
| 354 | " | " | H | OCHF₂ | CH₃ | CH | |
| 355 | " | " | H | OCHF₂ | CF₃ | CH | |
| 356 | " | " | H | OCHF₂ | OCHF₂ | CH | |
| 357 | SO₂C₂H₅ | OCH₂CH₂CH₃ | H | CH₃ | Cl | CH | |
| 358 | " | " | H | OCH₃ | Br | CH | |
| 359 | " | " | H | OCH₃ | NHCH₃ | CH | |
| 360 | " | " | H | OCHF₂ | OCH₃ | CH | |
| 361 | " | OCH(CH₃)₂ | H | CH₃ | CH₃ | CH | |
| 362 | " | " | H | OCH₃ | CH₃ | CH | |
| 363 | " | " | H | OCH₃ | OCH₃ | CH | |
| 364 | " | " | H | OCH₃ | Cl | CH | |
| 365 | " | " | H | OCHF₂ | CH₃ | CH | |
| 366 | " | O(CH₂)₃CH₃ | H | OCH₃ | NHCH₃ | CH | |
| 367 | " | " | H | OCHF₂ | OCH₃ | CH | |
| 368 | " | OCH₃ | H | OCHF₂ | CH₃ | CH | |
| 369 | " | " | H | OCHF₂ | CF₃ | CH | |
| 370 | " | " | H | OCHF₂ | OCHF₂ | CH | |
| 371 | " | " | H | CH₃ | Cl | CH | |

TABLE 2-continued $$R^1-Y-\underset{R^2}{N}-SO_2-NH-\underset{}{\overset{O}{C}}-\underset{R^3}{N}-\underset{N}{\overset{N}{\diagdown}}\underset{R^8}{\overset{R^7}{\diagdown}}E$$

| Ex. No. | —Y—R¹ | R² | R³ | R⁷ | R⁸ | E | M.p. (°C.) |
|---|---|---|---|---|---|---|---|
| 372 | " | " | H | OCH₃ | Br | CH | |
| 373 | " | " | H | OCH₃ | NHCH₃ | CH | |
| 374 | " | " | H | OCHF₂ | OCH₃ | CH | |
| 375 | " | O(CH₂)₃CH₃ | H | CH₃ | CH₃ | CH | |
| 376 | " | " | H | OCH₃ | CH₃ | CH | |
| 377 | " | " | H | OCH₃ | OCH₃ | CH | |
| 378 | " | " | H | OCH₃ | Cl | CH | |
| 379 | " | " | H | OCHF₂ | CH₃ | CH | |
| 380 | " | " | H | OCHF₂ | CF₃ | CH | |
| 381 | " | " | H | OCHF₂ | OCHF₂ | CH | |
| 382 | " | " | H | CH₃ | Cl | CH | |
| 383 | " | " | H | OCH₃ | Br | CH | |
| 384 | " | OC₆H₁₁ | H | CH₃ | CH₃ | CH | |
| 385 | " | " | H | OCH₃ | CH₃ | CH | |
| 386 | " | " | H | OCH₃ | OCH₃ | CH | |
| 387 | —SO₂C₂H₅ | OC₆H₁₁ | H | OCH₃ | Cl | CH | |
| 388 | " | " | H | OCHF₂ | CH₃ | CH | |
| 389 | " | " | H | OCHF₂ | CH₃ | CH | |
| 390 | " | " | H | OCHF₂ | OCHF₂ | CH | |
| 391 | " | " | H | CH₃ | Cl | CH | |
| 392 | " | " | H | OCH₃ | Br | CH | |
| 393 | " | " | H | OCH₃ | NHCH₃ | CH | |
| 394 | " | " | H | OCHF₂ | OCH₃ | CH | |
| 395 | —SO₂CH₃ | OC₃H₇ | H | CH₃ | CH₃ | CH | |
| 396 | " | " | H | OCH₃ | CH₃ | CH | |
| 397 | " | " | H | OCH₃ | OCH₃ | CH | |
| 398 | " | " | H | OCH₃ | Cl | CH | |
| 399 | " | " | H | OCHF₂ | CH₃ | CH | |
| 400 | " | " | H | OCHF₂ | CF₃ | CH | |
| 401 | " | " | H | OCHF₂ | OCHF₂ | CH | |
| 402 | " | " | H | CH₃ | Cl | CH | |
| 403 | " | " | H | OCH₃ | Br | CH | |
| 404 | " | " | H | OCH₃ | NHCH₃ | CH | |
| 405 | " | " | H | OCHF₂ | OCH₃ | CH | |
| 406 | " | OCH₂CH₃ | H | CH₃ | CH₃ | CH | |
| 407 | " | " | H | OCH₃ | CH₃ | CH | |
| 408 | " | " | H | OCH₃ | OCH₃ | CH | |
| 409 | " | " | H | OCH₃ | Cl | CH | |
| 410 | " | " | H | OCHF₂ | CH₃ | CH | |
| 411 | " | " | H | OCHF₂ | CF₃ | CH | |
| 412 | " | " | H | OCHF₂ | OCHF₂ | CH | |
| 413 | " | " | H | CH₃ | Cl | CH | |
| 414 | " | " | H | OCH₃ | Br | CH | |
| 415 | " | " | H | OCH₃ | NHCH₃ | CH | |
| 416 | " | " | H | OCHF₂ | OCH₃ | CH | |
| 417 | —SO₂CH₂CH₃ | OC₆H₅ | H | CH₃ | CH₃ | CH | |
| 418 | " | " | H | CH₃ | OCH₃ | CH | |
| 419 | " | " | H | OCH₃ | OCH₃ | CH | |
| 420 | " | " | H | OCH₃ | OCH₃ | N | |
| 421 | " | " | H | CH₃ | OCH₃ | N | |
| 422 | " | " | H | OCHF₂ | OCHF₂ | CH | |
| 423 | SO₂C₆H₅ | OCH₃ | H | CH₃ | CH₃ | CH | |
| 424 | " | " | H | CH₃ | OCH₃ | CH | |
| 425 | " | " | H | OCH₃ | OCH₃ | CH | 158–159 |
| 426 | " | " | H | OCH₃ | OCH₃ | N | |
| 427 | " | " | H | CH₃ | OCH₃ | N | |
| 428 | " | " | H | OCHF₂ | OCH₃ | CH | |
| 429 | SO₂N(CH₃)₂ | " | H | CH₃ | CH₃ | CH | |
| 430 | " | " | H | CH₃ | OCH₃ | CH | |
| 431 | " | " | H | OCH₃ | Cl | CH | |
| 432 | " | " | H | OCH₃ | OCH₃ | N | |
| 433 | " | " | H | CH₃ | OCH₃ | N | |
| 434 | " | " | H | OCHF₂ | OCHF₂ | CH | |
| 435 | " | OC₂H₅ | H | CH₃ | CH₃ | CH | |
| 436 | " | " | H | CH₃ | OCH₃ | CH | |
| 437 | " | " | H | OCH₃ | OCH₃ | CH | |
| 438 | " | " | H | OCH₃ | OCH₃ | N | |
| 439 | " | " | H | CH₃ | OCH₃ | N | |
| 440 | " | " | H | OCHF₂ | OCHF₂ | CH | |
| 441 | " | OC₃H₇(n) | H | OCH₃ | OCH₃ | CH | |
| 442 | " | " | H | OCH₃ | OCH₃ | N | |

TABLE 2-continued $$R^1-Y-\underset{R^2}{N}-SO_2-NH-\underset{}{\overset{O}{C}}-\underset{R^3}{N}-\underset{}{\text{ring}}\begin{matrix}N=\underset{R^7}{C}\\E\\N=\underset{R^8}{C}\end{matrix}$$

| Ex. No. | —Y—R$^1$ | R$^2$ | R$^3$ | R$^7$ | R$^8$ | E | M.p. (°C.) |
|---|---|---|---|---|---|---|---|
| 443 | " | " | H | CH$_3$ | OCH$_3$ | CH | |
| 444 | " | " | H | CH$_3$ | OCH$_3$ | N | |
| 445 | " | OC$_4$H$_9$(n) | H | OCH$_3$ | OCH$_3$ | CH | |
| 446 | " | " | H | OCH$_3$ | Cl | CH | |
| 447 | SO$_2$NHCH$_3$ | OCH$_3$ | H | OCH$_3$ | OCH$_3$ | CH | |
| 448 | " | " | H | OCH$_3$ | Cl | CH | |
| 449 | " | " | H | OCH$_3$ | CH$_3$ | CH | |
| 450 | " | " | H | CH$_3$ | CH$_3$ | CH | |
| 451 | " | " | H | CH$_3$ | OCH$_3$ | N | |
| 452 | " | " | H | OCH$_3$ | OCH$_3$ | N | |
| 453 | SO$_2$NHC$_2$H$_5$ | " | H | OCH$_3$ | OCH$_3$ | CH | |
| 454 | " | " | H | OCH$_3$ | Cl | CH | |
| 455 | " | " | H | OCH$_3$ | CH$_3$ | N | |
| 456 | " | " | H | OCH$_3$ | OCH$_3$ | N | |
| 457 | SO$_2$N⟨pyrrolidine⟩ | " | H | OCH$_3$ | OCH$_3$ | CH | |
| 458 | " | " | CH$_3$ | OCH$_3$ | OCH$_3$ | CH | |
| 459 | " | " | H | OCH$_3$ | CH$_3$ | CH | |
| 460 | SO$_2$N⟨piperidine⟩ | " | H | OCH$_3$ | CH$_3$ | CH | |
| 461 | " | " | H | OCH$_3$ | OCH$_3$ | CH | |
| 462 | SO$_2$C$_2$H$_5$ | " | CH$_3$ | OCH$_3$ | OCH$_3$ | CH | |
| 463 | " | " | CH$_3$ | OCH$_3$ | CH$_3$ | N | |
| 464 | SO$_2$N(CH$_3$)$_2$ | " | CH$_3$ | OCH$_3$ | OCH$_3$ | CH | |
| 465 | " | " | CH$_3$ | OCH$_3$ | CH$_3$ | N | |
| 466 | SO$_2$NHCH$_3$ | " | CH$_3$ | OCH$_3$ | OCH$_3$ | CH | |
| 467 | SOCH(CH$_3$)$_2$ | OC$_2$H$_5$ | H | OCH$_3$ | OCH$_3$ | CH | |
| 468 | " | " | H | OCH$_3$ | CH$_3$ | CH | |
| 469 | " | " | H | Cl | CH$_3$ | CH | |
| 470 | " | " | H | OCH$_3$ | OCH$_3$ | N | |
| 471 | SO$_2$CH$_3$ | OCH$_3$ | H | CH$_3$ | CH$_3$ | CH | 83–85 |
| 472 | " | " | H | OCH$_3$ | CH$_3$ | CH | 81–83 |
| 473 | " | " | H | OCH$_3$ | OCH$_3$ | CH | 142–144 |
| 474 | SO$_2$CH$_3$ | OCH$_3$ | H | OCH$_3$ | Cl | CH | |
| 475 | " | " | H | OCHF$_2$ | CH$_3$ | CH | |
| 476 | " | " | H | OCHF$_2$ | CF$_3$ | CH | |
| 477 | " | " | H | OCHF$_2$ | OCHF$_2$ | CH | |
| 478 | " | " | H | CH$_3$ | Cl | CH | |
| 479 | " | " | H | OCH$_3$ | Br | CH | |
| 480 | " | " | H | OCH$_3$ | NHCH$_3$ | CH | |
| 481 | " | " | H | OCHF$_2$ | OCH$_3$ | CH | |
| 482 | SO$_2$(n)C$_3$H$_7$ | " | H | CH$_3$ | CH$_3$ | CH | 115–118 |
| 483 | " | " | H | OCH$_3$ | CH$_3$ | CH | |
| 484 | " | " | H | OCH$_3$ | OCH$_3$ | CH | 163–165 |
| 485 | " | " | H | OCH$_3$ | Cl | CH | 143–145 |
| 486 | " | " | H | OCHF$_2$ | OCHF$_2$ | CH | |
| 487 | SO$_2$CH$_2$CH$_3$ | OCH$_2$CH$_3$ | H | CH$_3$ | CH$_3$ | CH | 148–150 |
| 488 | " | " | H | OCH$_3$ | CH$_3$ | CH | 142–144 |
| 489 | " | " | H | OCH$_3$ | OCH$_3$ | CH | 145–147 |
| 490 | " | " | H | OCH$_3$ | Cl | CH | |

BIOLOGICAL EXAMPLES

The damage to the weed plants, or the tolerance by the crop plants, was scored using a key in which the effectiveness is expressed by figures from 0 to 5. The figures denote:

0 = no effect
1 = 0 to 20% effect or damage
2 = 20 to 40% effect or damage
3 = 40 to 60% effect or damage
4 = 60 to 80% effect or damage
5 = 80 to 100% effect or damage

1. Pre-emergence effect on weeds

Seeds or rhizome pieces of monocotyledon and dicotyledon weed plants were placed in sandy loam soil in plastic pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effect on the emergence was scored visually after a test period of 3 to 4 weeks by comparison with untreated controls. As shown by the score figures in Table 3, the compounds according to the invention have a good herbicidal pre-emergence action against a broad range of grass weeds and dicotyledon weeds.

TABLE 3

Pre-emergence action of the compounds of the formula (I) according to the invention

| Example No. | Dose (kg of a.i./ha) | Herbicidal action | | | |
|---|---|---|---|---|---|
| | | STM | CRS | SIA | LOM |
| 24 | 0.3 | 5 | 5 | 1 | 2 |
| 25 | 0.3 | 5 | 5 | 4 | 4 |
| 105 | 0.3 | 5 | 5 | 5 | 3 |
| 106 | 0.3 | 5 | 5 | 5 | 4 |
| | 0.08 | 5 | 5 | 5 | 4 |
| 107 | 0.3 | 4 | 3 | 3 | 1 |
| 165 | 0.3 | 5 | 2 | 2 | 2 |
| 166 | 0.3 | 5 | 3 | 4 | 3 |
| 225 | 0.3 | 5 | 5 | 4 | 4 |
| 226 | 0.3 | 5 | 3 | 1 | 1 |
| 231 | 0.3 | 5 | 5 | 5 | 5 |
| 232 | 0.3 | 5 | 5 | 5 | 5 |
| 237 | 0.3 | 5 | 5 | 5 | 5 |
| 238 | 0.3 | 4 | 4 | 1 | 2 |
| 347 | 0.3 | 5 | 5 | 5 | 5 |
| 348 | 0.3 | 5 | 5 | 5 | 5 |
| 425 | 0.3 | 2 | 2 | 3 | 1 |
| 471 | 0.3 | 2 | 4 | 5 | 2 |
| 472 | 0.3 | 5 | 5 | 5 | 3 |
| 473 | 0.3 | 5 | 5 | 5 | 5 |
| 482 | 0.3 | 1 | 4 | 5 | 1 |
| 484 | 0.3 | 5 | 5 | 5 | 4 |
| 485 | 0.3 | 2 | 4 | 5 | 2 |
| 488 | 0.3 | 5 | 5 | 5 | 5 |

STM = Stellaria media
CRS = Chrysanthemum segetum
SIA = Sinapis alba
LOM = Lolium multiflorum

2. Post-emergence effect on weeds

Seeds or rhizome pieces of monocotyledon and dicotyledon weeds were placed in sandy loam soil in plastic pots, covered with soil and grown in a greenhouse under good growth conditions Three weeks after sowing, the test plants were treated in the three-leaf stage.

The compounds according to the invention which were formulated as wettable powders or as emulsion concentrates were sprayed in various dosages on the green parts of the plants at an application rate of 600 to 800 l of water/ha (converted) and, after the test plants had remained in the greenhouse for about 3 to 4 weeks under ideal growth conditions, the effect of the preparations was scored visually by comparison with untreated controls.

The agents according to the invention also have a good herbicidal post-emergence action against a broad range of economically important grass weeds and dicotyledon weeds (Table 4).

TABLE 4

Post-emergence effect of the compounds of the formula (I) according to the invention

| Example No. | Dose (kg of a.i./ha) | Herbicidal action | | | |
|---|---|---|---|---|---|
| | | STM | CRS | SIA | LOM |
| 24 | 0.3 | 4 | 2 | 2 | 0 |
| 25 | 0.3 | 5 | 5 | 4 | 0 |
| 105 | 0.3 | 5 | 4 | 4 | 1 |
| 106 | 0.3 | 5 | 5 | 5 | 1 |
| | 0.08 | 5 | 5 | 5 | 1 |
| 107 | 0.3 | 5 | 2 | 2 | 0 |
| 165 | 0.3 | 5 | 2 | 3 | 0 |
| 166 | 0.3 | 5 | 4 | 4 | 2 |
| 225 | 0.3 | 5 | 4 | 4 | 0 |
| 226 | 0.3 | 4 | 1 | 4 | 1 |
| 231 | 0.3 | 5 | 5 | 1 | 2 |
| 232 | 0.3 | 5 | 3 | 4 | 3 |
| 237 | 0.3 | 5 | 4 | 5 | 3 |
| 238 | 0.3 | 5 | 2 | 3 | 0 |
| 347 | 0.3 | 5 | 5 | 5 | 4 |
| 348 | 0.3 | 5 | 5 | 5 | 4 |
| 425 | 0.3 | 3 | 2 | 4 | 1 |
| 472 | 0.3 | 5 | 4 | 5 | 3 |
| 473 | 0.3 | 5 | 5 | 5 | 2 |
| 482 | 0.3 | 4 | 5 | 5 | 1 |
| 484 | 0.3 | 4 | 4 | 5 | 3 |
| 485 | 0.3 | 1 | 2 | 5 | 1 |
| 488 | 0.3 | 4 | 5 | 5 | 3 |

Abbreviations: See Table 3

3. Tolerance by crop plants

In further greenhouse experiments, seeds of a substantial number of crop plants and weeds were placed in sandy loam soil and covered with soil.

Some of the pots were treated immediately as described under 1., and the remaining pots were placed in a greenhouse until the plants had developed two to three leaves and then sprayed with various dosages of the substances according to the invention as described under 2.

Visual scoring four to five weeks after the application and after the plants had been in the greenhouse revealed that the compounds according to the invention did not inflict any damage to dicotyledon crops such as, for example, soya, cotton, oilseed rape, sugar beet and potatoes when used pre- and post-emergence, even when high dosages of active substance were used. Moreover, some substances also left Gramineae crops such as, for example, barley, wheat, rye, Sorghum species, maize or rice unharmed. The compounds of the formula (I) therefore have a high selectivity when used for controlling undesired plant growth in agricultural crops.

4. Inhibition of growth in cereals

In tray experiments in the greenhouse, young cereal plants (wheat, barley, rye) in the 3-leaf stage were sprayed to runoff point with compounds according to the invention in various concentrations of active substance (kg/ha).

After the untreated control plants had reached a length of about 55 cm, the additional growth of all plants was measured, and the inhibition of growth was calculated as a percentage of the additional growth of the control plants. The phytotoxic effect of the compounds was also determined, with 100% denoting that growth had ceased and 0% denoting a growth corresponding to that of the untreated control plants. It emerged that the compounds have very good growth-regulating properties.

We claim:

1. A compound of the general formula (I)

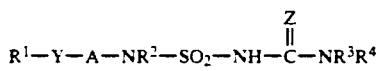

where
- A is a direct bond or a saturated or unsaturated, unbranched or branched $C_1$-$C_{10}$-hydrocarbon radical,
- $R^1$ is $C_1$-$C_8$-alkyl, $C_2$-$C_8$-alkenyl, $C_2$-$C_8$-alkynyl, $C_3$-$C_8$-cycloalkyl, $C_5$-$C_8$-cycloalkenyl, or one of the above five radicals which is monosubstituted or polysubstituted by halogen or by those radicals which are selected from the group comprising $C_1$-$C_8$-alkoxy, $C_2$-$C_6$-alkenyloxy, $C_2$-$C_6$-alkynyloxy, $C_1$-$C_6$-alkylthio, $C_1$-$C_6$-alkylsulfinyl, $C_1$-$C_6$-alkylsulfonyl, $C_3$-$C_6$-cycloalkyl, a radical of a three-membered to six-membered saturated heterocycle with one oxygen atom in the ring, furyl, phenyl and a phenyl radical which is monosubstituted or polysubstituted by radicals from the group comprising halogen, CN, $C_1$-$C_4$-alkyl, $C_1$-$C_4$-alkoxy, $C_1$-$C_4$-haloalkyl, or by ($C_1$-$C_4$-alkoxy)carbonyl and nitro, or phenyl or a phenyl radical which is monosubstituted or polysubstituted by radicals from the group embracing halogen, $C_1$-$C_4$-alkyl, $C_1$-$C_4$-alkoxy, $C_1$-$C_4$-haloalkyl, or by ($C_1$-$C_4$-alkoxy)carbonyl and nitro, or phenyl or a radical of the formula —$NR^5R^6$, where $R^5$ and $R^6$ independently of one another are hydrogen or $C_1$-$C_8$-alkyl, or one of the radicals $R^5$ and $R^6$ is $C_1$-$C_4$-alkoxy, or $R^5$ and $R^6$ together form an alkylene chain —$(CH_2)_n$— with n being 2 to 7;
- Y is S, SO or $SO_2$
- $R^2$ is $C_1$-$C_8$-alkyloxy, $C_2$-$C_8$-alkenyloxy, $C_2$-$C_8$-alkynyloxy or one of the above 3 radicals which is monosubstituted or polysubstituted by halogen or by radicals from the group comprising $C_1$-$C_6$-alkoxy, $C_2$-$C_8$-alkenyloxy, $C_2$-$C_6$-alkynyloxy, $C_1$-$C_6$-alkylthio, $C_1$-$C_6$-alkylsulfinyl, $C_1$-$C_6$-alkylsulfonyl, ($C_1$-$C_6$-alkoxy)carbonyl, phenoxycarbonyl, benzyloxycarbonyl and phenyl, or $R^2$ is $C_3$-$C_8$-cycloalkyloxy which is unsubstituted or monosubstitutedor polysubstituted by halogen, or monosubstituted or disubstituted by halogen, or monosubstituted or disubstituted by $C_1$-$C_4$-alkoxy or $C_1$-$C_4$-alkylthio; $C_5$-$C_8$-cycloalkenyloxy, cyclopropylmethyloxy, epoxypropyloxy, furfuryloxy, tetrahydrofurfuryloxy, phenoxy-$C_1$-$C_6$-alkyloxy, phenoxy or one of the last two abovementioned radicals which is substituted in the phenyl ring by halogen, $C_1$-$C_4$-alkyl, $C_1$-$C_4$-alkoxy or nitro, is H, $C_1$-$C_8$-alkyl, $C_2$-$C_8$-alkenyl, $C_2$-$C_8$-alkynyl or $C_1$-$C_4$-alkoxy,
- $R^4$ is a radical of the formula

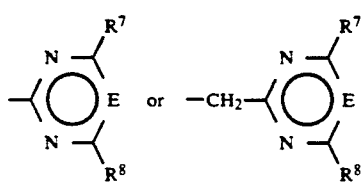

$R^7$ and $R^8$ independently of one another are H, halogen, $C_1$-$C_6$-alkyl, $C_1$-$C_6$-alkoxy, $C_1$-$C_6$-alkylthio or one of the last three abovementioned radicals which is monosubstituted or polysubstituted by halogen or monosubstitutedor disubstituted by $C_1$-$C_4$-alkoxy or $C_1$-$C_4$-alkylthio, or are a radical $NR^{13}R^{14}$, $C_3$-$C_6$-cycloalkyl, —$OCHR^{15}COOR^{16}$, $C_3_1$-$C_5$-alkenyl, $C_2$-$C_4$-alkynyl, $C_3$-$C_5$-alkenyloxy or $C_3$-$C_5$-alkynyloxy,
- $R^{13}$ and $R^{14}$ independently of one another are H, $C_1$-$C_4$-alkyl, $C_2$-$C_4$-alkenyl or $C_3$-$C_4$-alkynyl,
- $R^{15}$ is hydrogen or $C_1$-$C_4$-alkynyl,
- $R^{16}$ is hydrogen or $C_1$-$C_4$-alkyl,
- E is CH, and
- Z is O or S, and salts thereof.

2. A compound of the formula (I) and a salt thereof as claimed in claim 1, wherein A is a direct bond or a divalent radical of the formula $CH_2CH_2$, CRR', $CH_2CHR$ or $CH_2CRR'$, where R and R' independently of one another are $C_1$-$C_4$-alkyl or $C_2$-$C_4$-alkenyl.

3. A compound of the formula (I) and a salt thereof as claimed in claim 1, wherein $R^1$ is $C_1$-$C_4$-alkyl, a $C_1$-$C_4$-alkyl radical which is monosubstituted or polysubstituted by halogen or monosubstituted or disubstituted by $C_1$-$C_4$-alkoxy, $C_2$-$C_3$-alkenyloxy, $C_2$-$C_3$-alkynyloxy, $C_1$-$C_4$-alkylthio, $C_1$-$C_4$-alkylsulfinyl, $C_1$-$C_4$-alkylsulfonyl, phenyl or a phenyl radical which is monosubstituted to trisubstituted by radicals from the group comprising halogen, $C_1$-$C_4$-alkyl, $C_1$-$C_4$-alkoxy, $CF_3$, ($C_1$-$C_4$-alkoxy)carbonyl and nitro, or are $C_3$-$C_8$-cycloalkyl or a $C_3$-$C_8$-cycloalkyl radical which is monosubstituted or polysubstituted by halogen or monosubstituted to disubstituted by $C_1$-$C_4$-alkoxy or $C_1$-$C_4$-alkylthio, or $R^1$ is $C_5$-$C_8$-cycloalkenyl, cyclopropylmethyl, epoxypropyl, furfuryl, tetrahydrofurfuryl, benzyl, phenyl, or is a benzyl or phenyl radical which is substituted in the phenyl ring by one or more radicals from the group comprising halogen, $C_1$-$C_4$-alkyl, $C_1$-$C_4$-alkoxy, $CF_3$, ($C_1$-$C_4$-alkoxy)carbonyl and nitro, or $R^1$ is a radical of the formula $NR^5R^6$, where $R^5$ is $C_1$-$C_4$-alkyl and $R^6$ is hydrogen or $C_1$-$C_4$-alkyl, or $R^5$ and $R^6$ together form an alkylene chain —$(CH_2)_n$— with n being 4 or 5.

4. A compound of the formula (I) and a salt thereof as claimed in claim 1, wherein $R^2$ is $C_1$-$C_4$-alkyloxy, a $C_1$-$C_4$-alkyloxy radical which is monosubstituted or polysubstituted by halogen order monosubsituted or disubstituted by $C_1$-$C_4$-alkoxy, $C_2$-$C_4$-alkenyloxy, propargyloxy, $C_1$-$C_4$-alkylthio, $C_1$-$C_4$-alkylsulfonyl, $C_1$-$C_4$-alkylsulfonyl, ($C_1$-$C_4$-alkoxy)carbonyl, phenoxycarbonyl, benzyloxy-carbonyl or phenyl, or is $C_3$-$C_8$-cycloalkyloxy.

5. A compound of the formula (I) and a salt thereof as claimed in claim 1, wherein $R^4$ is a radical of the formula

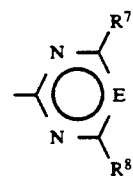

and $R^7$ and $R^8$ independently of one another are halogen, $C_1$-$C_4$-alkyl, $C_1$-$C_4$-alkoxy, $C_1$-$C_4$-alkylthio or one of the last three abovementioned radicals which are monosubstituted or polysubstituted by halogen or monosubstituted or disubstituted by $C_1$-$C_4$-alkoxy or $C_1$-$C_4$-alkylthio, or $R^7$ and $R^8$ are a radical $NR^{13}R^{14}$, $C_3$-$C_8$-cycloalkyl, —OCHR$^{15}$COOR$^{16}$, allyl, propargyl, allyloxy or propargyloxy, $R^{13}$ and $R^{14}$ independently of one another are H or $C_1$-$C_4$-alkyl, $R^{15}$ is H or $C_1$-$C_4$-alkyl, $R^{16}$ is $C_1$-$C_4$-alkyl, and E is CH or N.

6. A compound of the formula (I) and a salt thereof as claimed in claim 1, wherein A is a direct bond, $R^1$ is $C_1$-$C_4$-alkyl, a $C_1$-$C_4$-alkyl radical which is monosubstituted or polysubstituted by halogen or monosubstituted to disubstituted by $C_1$-$C_4$-alkoxy, or is a radical of the formula $NR^5R^6$ where $R^5$ is $C_1$-$C_4$-alkyl and $R^6$ is hydrogen or $C_1$-$C_4$-alkyl or $R^5$ and $R^6$ together form an alkylene chain —(CH$_2$)$_n$— with n being 4 or 5, $R^2$ is $C_1$-$C_4$-alkoxy which is unsubstituted or monosubstituted or polysubstituted by halogen or by ($C_1$-$C_4$-alkoxy)carbonyl, phenoxycarbonyl, benzyloxycarbonyl or phenyl, $R^3$ is H, $C_1$-$C_4$-alkyl or allyl, $R^4$ is a radical of the formula

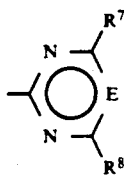

$R^7$ and $R^8$ independently of one another are halogen, $C_1$-$C_4$-alkyl, $C_1$-$C_4$-alkoxy or one of the last two abovementioned radicals which is halogenated, E is CH, and Z is an oxygen atom.

7. A compound as claimed in claim 6, wherein Y is SO$_2$, $R^1$ is methyl, ethyl or dimethylamino, $R^2$ is methoxy or ethoxy, $R^3$ is H, $R^7$ is methoxy or methyl and $R^8$ is methoxy or methyl.

8. A compound of the formula (I) and a salt thereof as claimed in claim 1, wherein A is a radical of the formula —CH$_2$—CH$_2$—, $R^1$ is $C_1$-$C_4$-alkyl, a $C_1$-$C_4$-alkyl radical which is monosubstituted or polysubstituted by halogen or monosubstituted to disubstituted by $C_1$-$C_4$-alkoxy, or is $C_3$-$C_8$-cycloalkyl which is unsubstituted or monosubstituted or polysubstituted by halogen, or is benzyl, phenyl or a benzyl or phenyl radical which is monosubstituted or polysubstituted in the phenyl ring by halogen, $C_1$-$C_4$-alkyl, $C_1$-$C_4$-alkoxy, CF$_3$, ($C_1$-$C_4$-alkoxy)carbonyl or nitro, $R^2$ is $C_1$-$C_4$-alkoxy which is unsubstituted or monosubstituted or polysubstituted by halogen or by ($C_1$-$C_4$-alkoxy)carbonyl, phenyloxycarbonyl, benzyloxycarbonyl or phenyl, $R^3$ is H, $C_1$-$C_4$-alkyl or allyl, $R^4$ is a radical of the formula

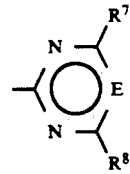

$R^7$ and $R^8$ independently of one another are halogen, $C_1$-$C_4$-alkyl, $C_1$-$C_4$-alkoxy or one of the last two abovementioned radicals which is halogenated, E is CH, and Z is O or S.

9. A compound as claimed in claim 8, wherein Z is O, Y is SO$_2$, $R^1$ is methyl, ethyl, or dimethylamino, $R^2$ is methoxy or ethoxy, $R^3$ is H, $R^7$ is methoxy or methyl and $R^8$ is methoxy or methyl.

10. A compound as claimed in claim 9, wherein $R^1$ is methyl, $R^2$ is methoxy, $R^7$ is methoxy and $R^8$ is methoxy.

11. A compound as claimed in claim 9, wherein $R^1$ is ethyl, $R^2$ is methoxy, $R^7$ is methoxy and $R^8$ is methoxy.

12. A compound as claimed in claim 9, wherein $R^1$ is ethyl, $R^2$ is methoxy, $R^7$ is methoxy and $R^8$ is methyl.

13. A compound as claimed in claim 9, wherein $R^1$ is methyl, $R^2$ is ethoxy, $R^7$ is methoxy and $R^8$ is methyl.

14. A compound as claimed in claim 9, wherein $R^1$ is methyl, $R^2$ is ethoxy, $R^7$ is methoxy and $R^8$ is methyl.

15. A compound as claimed in claim 9, wherein $R^1$ is ethyl, $R^2$ is ethoxy, $R^7$ is methoxy and $R^8$ is methoxy.

16. A compound as claimed in claim 9, wherein $R^1$ is dimethylamino, $R^2$ is methyl, $R^7$ is methyl and $R^8$ is methoxy.

17. A compound as claimed in claim 9, wherein $R^1$ is dimethylamino, $R^2$ is methyl, $R^7$ is methoxy and $R^8$ is methoxy.

18. A herbicidal or plant-growth-regulating composition which contains a compound of the formula (I) or salt thereof as claimed in claim 1, in addition to inert carrier substances.

19. A process for selectively combatting undesirable plants or for regulating plant growth which comprises applying an effective amount of a compound of the formula (I) or a salt thereof as claimed in claim 1 onto the plants, seeds or the area where the plants grow.

* * * * *

UNITED STATES PATENT AND TRADEMARK OFFICE
CERTIFICATE OF CORRECTION

PATENT NO. : 5,129,941
DATED : July 14, 1992
INVENTOR(S) : Loher et al.

It is certified that error appears in the above-identified patent and that said Letters Patent is hereby corrected as shown below:

Column 29, line 48, replace "monosubstitutedor" with "monosubstituted or";

Column 29, line 56, before "is" insert "$R^3$";

Column 30, line 5, replace "monosubstitutedor" with "monosubstituted or";

Column 30, line 8, after "$C_3$" delete "1";

Column 30, line 12, change "alkynyl" to "alkyl".

Column 30, line 49, change "alkylsulfonyl" to "alkylsulfinyl".

Column 31, line 4-5, replace "$-OCHR^1_5COOR^{16}$" with "$-OCHR^{15}-COOR^{16}$".

Column 31, line 11, delete "or N".

Signed and Sealed this

Seventh Day of June, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,129,941

DATED : July 14, 1992

INVENTOR(S) : Loher et al.

It is certified that error appears in the above-identified patent and that said Letters Patent is hereby corrected as shown below:

Column 30, line 47, replace "order" with "or"; and

Column 32, line 35, after "$R^8$ is" replace "methyl" with "methoxy".

Signed and Sealed this

Twentieth Day of September, 1994

Attest:

Attesting Officer

BRUCE LEHMAN

Commissioner of Patents and Trademarks